(12) United States Patent
Benlloch Baviera et al.

(10) Patent No.: US 9,072,451 B2
(45) Date of Patent: Jul. 7, 2015

(54) COMPACT, HYBRID AND INTEGRATED GAMMA/RF SYSTEM USED TO FORM SIMULTANEOUS PET OR SPECT AND MR IMAGES

(75) Inventors: José Maria Benlloch Baviera, Paterna (ES); Filomeno Sánchez Martínez, Paterna (ES); Ángel Martínez-Garrido Martínez, Paterna (ES); Lourdes Martinez Valero, legal representative, Valencia (ES); Vincente Belloch Ugarte, Valencia (ES); Noriel Pavón Hernández, Valencia (ES); Luis Caballero Ontanaya, Valencia (ES); Christoph Lerche, Valencia (ES); Ángel Sebastiá Cortés, Valencia (ES)

(73) Assignees: CONSEJO SUPERIOR DE INVESTIGACIONES CIENTIFICAS, Madrid (ES); UNIVERSIDAD DE VALENCIA, Valencia (ES)

( * ) Notice: Subject to any disclaimer, the term of this patent is extended or adjusted under 35 U.S.C. 154(b) by 1000 days.

(21) Appl. No.: 13/143,579

(22) PCT Filed: Jan. 7, 2010
(Under 37 CFR 1.47)

(86) PCT No.: PCT/ES2010/070004
§ 371 (c)(1),
(2), (4) Date: Feb. 10, 2012

(87) PCT Pub. No.: WO2010/079251
PCT Pub. Date: Jul. 15, 2010

(65) Prior Publication Data
US 2012/0136237 A1      May 31, 2012

(30) Foreign Application Priority Data

Jan. 7, 2009  (ES) .................................. 200900037

(51) Int. Cl.
A61B 5/05      (2006.01)
A61B 5/055     (2006.01)
(Continued)

(52) U.S. Cl.
CPC ................. *A61B 5/055* (2013.01); *A61B 6/037* (2013.01); *A61B 6/5247* (2013.01);
(Continued)

(58) Field of Classification Search
None
See application file for complete search history.

(56) References Cited

U.S. PATENT DOCUMENTS

| 4,939,464 A | 7/1990 | Hammer |
| 6,362,479 B1 | 3/2002 | Andreaco |

(Continued)

FOREIGN PATENT DOCUMENTS

| JP | 2001149351 | 6/2001 |
| JP | 2002052014 | 2/2002 |

OTHER PUBLICATIONS

Schlyer et al. "A Simultaneous PET/MRI Scanner Based on RatCAP in Small Animals." 2007 IEEE Nuclear Science Symposium Conference Record. pp. 3256-3259.*

(Continued)

*Primary Examiner* — James Kish
(74) *Attorney, Agent, or Firm* — Merchant & Gould P.C.

(57) ABSTRACT

The GAMMA/RF compact, hybrid and integrated system for PET-SPECT/MR simultaneous imaging of the invention comprises a GAMMA/RF device that integrates an RF coil, of the type used in conventional MR systems, with GAMMA radiation detector modules of the type used in PET or SPECT systems, so that combined PET or SPECT and MR images are obtained.

20 Claims, 6 Drawing Sheets

(51) Int. Cl.
*A61B 6/03* (2006.01)
*A61B 6/00* (2006.01)
*G01R 33/34* (2006.01)
*G01R 33/48* (2006.01)
*G01T 1/16* (2006.01)

(52) U.S. Cl.
CPC ....... *G01R 33/34046* (2013.01); *G01R 33/481* (2013.01); *G01T 1/1603* (2013.01); *A61B 6/4417* (2013.01); *A61B 6/508* (2013.01)

(56) References Cited

U.S. PATENT DOCUMENTS

| | | | |
|---|---|---|---|
| 6,858,847 | B1 | 2/2005 | Macciocchi |
| 2005/0098844 | A1* | 5/2005 | Sandvik et al. ............... 257/438 |
| 2006/0250133 | A1 | 11/2006 | Krieg |
| 2006/0293580 | A1* | 12/2006 | Ladebeck et al. ............. 600/407 |
| 2008/0208044 | A1* | 8/2008 | Lecoq et al. ................. 600/436 |
| 2008/0265887 | A1 | 10/2008 | Linz |
| 2008/0284428 | A1* | 11/2008 | Fiedler et al. ................. 324/307 |
| 2009/0270718 | A1* | 10/2009 | Peter et al. .................... 600/411 |

OTHER PUBLICATIONS

Vaska et al., "RatCAP: Miniaturized Head-Mounted PET for Conscious Rodent Brain Imaging." 2004, IEEE, pp. 1780-1784.*
Cherry, "Multimodality in vivo imaging systems: twice the power or double the trouble?" Ann. Rev. Biomed. Eng, (2006) 8: 35-62.
International Search Report for corresponding International Application No. PCT/ES2010/070004.
Written Opinion for corresponding International Application No. PCT/ES2010/070004.
International Preliminary Examination Report for corresponding International Application No. PCT/ES2010/070004.

* cited by examiner

COMPACT, HYBRID AND INTEGRATED GAMMA/RF SYSTEM USED TO FORM SIMULTANEOUS PET OR SPECT AND MR IMAGES

PRIORITY

This application is a National Stage Application of PCT/ES2010/070004, filed Jan. 7, 2010, which claims priority to Spanish patent application P200900037, filed Jan. 7, 2009 and which applications are incorporated herein by reference. To the extent appropriate, a claim of priority is made.

OBJECT OF THE INVENTION

The main object of the present invention falls within the field of medicine, and in particular is directed to a new system that combines a radio frequency coil (RF) of the type used in conventional magnetic resonance (MR) units with GAMMA radiation detectors of the type used in Positron Emission Tomography (PET) units. The result is a GAMMA/RF hybrid system that allows obtaining images simultaneously through PET or SPECT and MR techniques.

BACKGROUND OF THE INVENTION

The medical image comprises a set of widely used techniques for diagnosis and treatment of disease. The type of image obtained can be morphological (Computed Axial Tomography (CT), Magnetic Resonance Imaging (MRI), X-ray, ultrasound, etc.) or functional (GAMMA camera, positron and single photon emission, positron emission tomography or PET, etc).

Nuclear Medicine is a medical specialty in which functional images are obtained using ionizing radiation. Tracers are biomolecules previously labeled with radionuclide, which are concentrated preferentially in a particular area of interest (organs, bones, tissues). This area of interest then emits GAMMA radiation, which is received by a detection system (usually a scintillator crystal) designed to transform incident GAMMA radiation energy into light. This light, in turn, is detected by photosensitive elements (usually photomultiplier tubes), so that it is possible to calculate and store the position at which the GAMMA radiation emission was produced. Thus, the distribution of tracers is determined and an image of the organ, tissue or body of the subject under study, is obtained.

Positron Emission Tomography (PET), which is a noninvasive technique with high sensitivity, falls within the Nuclear Medicine field. The PET technique allows obtaining live images of the distribution of positron-emitting tracers that produce, after their annihilation, the emission of two photons in opposite directions and of the same energy (511 keV). This technique measures peak molar concentrations of the tracer. The most widely used PET tracer is FDG (fluordeoxiglucose), similar to the glucose molecule. FDG accumulates in cells with a high metabolism, such as cancer cells, being visualized through PET tumors and metastases in the early state, long before morphological changes that can be detected with other techniques such as magnetic resonance, CT, etc, occur. In addition to cancer, PET is useful in studying the functioning of certain organs like the heart, brain, circulatory system and lungs. U.S. Pat. No. 6,858,847 describes an example of the type of instrumentation and methodology involved in PET technology.

However, PET technique has limitations that are directly related to the physical properties of the positron and statistics (number of events detected for the image) of the measure. These limitations are sometimes responsible for PET imaging holding a significant deficiency in terms of anatomical information, and it is otherwise difficult to locate the exact position in which the accumulation of the radioactive tracer occurs.

The need to obtain both good anatomical and functional resolution drove to the development of systems that combine PET and CT technology in one device in the 1990's. Its use quickly spread and is now routinely used in medical diagnosis, thus demonstrating the advantages in obtaining integrated anatomical and molecular images. The way in which this integration took place was simply by placing the PET and CT one after another in a setting like a "tandem". In this way the system integrates mainly via "software", since at the "hardware" level very few changes are required. Once operational, the PET/CT system acquires data sequentially through a stretcher that moves along both scanners.

On the other hand, Magnetic Resonance Imaging (MR), also called nuclear magnetic resonance (NMR) is based on the excitation and detection of the precession of magnetic moments, in the range of the radio frequency, of the atomic nucleus, primarily of hydrogen ($^1H$), the object under investigation, along with its phase variation, frequency and location. MRI (magnetic resonance imaging) is based on spatial encoding of the resonance signal, while the interest of the MRS (magnetic resonance spectroscopy) focuses on the chemical environment of the nucleus.

Current MRI systems most widely used are composed of three basic elements:

1) A cylindrical magnet which produces a high magnetic field (typically 1.5 or 3 Tesla) and uniform (B0).

2) A gradient coil system which slightly modifies the BO field in spatial directions X, Y and Z in order to encode the position of the signal.

3) A Radio Frequency field within the gradient field produced by an RF coil (or a combination of RF coils) that sends and receives signals. These MR systems are able to obtain images of any part of the body and even the whole body, although in this case their production is very slow. This system includes an RF shielding that prevents the coupling of the RF coil with the other components of the MR system or any other additional equipment.

The three previous elements are placed in a conventional magnetic resonance unit following a toroidal shape in the following order (inside out in the radial direction): the RF coil, the gradient coils system and the cylindrical magnet. The patient to be examined is placed in the hollow interior of the cylinder, on a mobile stretcher and adjusting its position to be able to perform the measure on the body area being studied. In studies with animals or phantoms there are other possibilities for positioning.

Sometimes a high quality image of a particular body region is needed. In such cases, a specific portable RF coil placed near the area of interest is used. For example, in order to obtain an image of the brain with high sensitivity an RF cylindrical coil with an internal diameter of about 26 cm is placed around the head.

Compared with CT, MR generally provides greater soft tissue contrast and superior spatial resolution in anatomical images, with an immediate impact on clinical practice by allowing a better diagnosis in diseases of the brain, pelvis, liver and locomotion system (skeletal-muscle). In addition to the morphological image, the MR also provides important information about physiological parameters (diffusion, permeability, BOLD) from differences in relaxation times of nuclei $^1H$ (which is usually referred to as "protons") which are located in different biochemical substances. Finally, the addition of passive contrast agents based on gadolinium or iron oxide nanoparticles can significantly increase the contrast in the MR. The combination of MRI techniques allows visualizing the anatomical morphological consequences (tumor growth, brain atrophy, abnormalities in heart wall, vascular anatomy, neuronal activation and acute stroke) of many diseases both in humans and in animal models.

There is great synergy between PET, (SPECT) and MR techniques, as each of them separately provides information that is not possible to obtain with the other. The possibility of obtaining metabolic, physiological or molecular images using PET technique and being able to relate them directly to the images of exceptional anatomical quality obtained with MR technique opens a vast field of possibilities. This is the reason why these techniques are combined in clinical diagnostics and research (etiology and evolution of human diseases in animal models, pre-clinical evaluation of drug kinetics and drug-dynamics of new therapeutic strategies, peptides and antibodies, cell therapy, gene therapy and nanoparticle based therapies).

Technological and practical development problems in these PET/MR systems are much more complex than in PET/CT systems, and for that reason, images of PET and MR are usually currently acquired in physically separated systems in a sequential way. Subsequently, both images are merged through a specific software that makes use of the information contained in the image itself ("landmarks") or of external fiducial markers that can be clearly identified in the two images that are intended to be merged.

However, this method of obtaining images from a combination of MR and PET techniques is inappropriate in the study of organs with their own physiological movement, such as the stomach, intestines and heart. On the other hand, the sequential acquisition of PET and MR images does not allow PET/MR dynamic temporarily correlated studies that are necessary on numerous occasions. Biological systems are inherently dynamic and their response to certain drugs and contrast agents has a strong time dependence. The timescale of these changes varies from seconds to minutes.

Therefore, it is extremely important to have a "multimodal" system within a same unit capable of registering PET and MR images simultaneously, thus ensuring that the patient is studied in the same physiological state and, therefore, correlating the temporal changes at the same time in both PET and MR in response to a disturbance. U.S. Pat. No. 4,939,464 already describes a system that combines PET and MR in a single unit.

The main reason why it is complex, from a technological point of view, to unify PET and MR techniques, is the interference of the PET system with magnetic fields of all types, as well as interferences from the resonance radio frequency (both excitation and detection) with the PET electronics.

Another drawback is that the MR behavior can be affected by the presence of the elements used in PET, such as detectors or associated electronics, especially drivers and ferromagnetic materials as they modify the properties of the static magnetic field and the RF field distribution, respectively. For this reason, S. R. Cherry has proposed to avoid the use of conductive or ferromagnetic materials in the inner part of PET (Cherry S. R 2006, Multimodality in vivo imaging systems: twice the power or double the trouble? Ann. Rev. Biomed. Eng. 8 35).

DESCRIPTION

The GAMMA/RF compact, hybrid and integrated system for PET-SPECT/MR simultaneous imaging of the invention comprises a device that integrates an RF coil, in particular of the type used to take images of specific parts of a patient in conventional MR systems, with GAMMA radiation detector modules of the type used in PET or SPECT systems, so that the obtaining of combined PET-SPECT with MR images is optimized. That is, the images obtained by the system of the invention provide morphological information (MR) and functional information (PET or SPECT). The MR structural high definition and the metabolic information provided by PET-SPECT can achieve a better diagnosis than either of them alone. It is understood that the GAMMA system of the present document is able to detect two GAMMA rays in opposition, in the case of the PET modality, as a single GAMMA ray, in the case of the SPECT modality.

In addition, a further advantage of this GAMMA/RF system is that it can be implemented in a portable device. Current hybrid systems are integrated permanently into MR whole body units, can not be adjusted for specific applications and can not be used as an addition to a single-mode MR system. This invention, in its portable form, has the ability to improve existing resonance systems by GAMMA detection mode, obtaining a dual-mode PET-SPECT/MR system with true simultaneous detection. Thus, a conventional MR system can be used as such, with the possibility that it can be changed to PET-SPECT/MR mode at any time and return to MR mode later. This reduces the PET-SPECT/MR system cost significantly and makes it much more affordable for facilities that already have a conventional MR system, including both clinical and research centers for humans or animals. Therefore, an important advantage of the present invention, in its portable version, is the ability to improve current MR systems using a simple upgrade. There are thousands of MR systems installed around the world that are very expensive. The present invention avoids the replacement of said systems by others even more expensive that operate in PET-SPECT/MR dual mode, with the introduction of the hand-held GAMMA/RF device as a potential addition. In this way, we get a multi modal diagnostic system that combines anatomical and functional information into a single merged image.

The main drawback of combining an RF coil with GAMMA detectors is that the RF radiation adversely affects the GAMMA electronic detection which is why it is essential to have an RF shield between the RF coil and said GAMMA electronic detection. However, only the RF should be shielded but not the photons from the scintillator crystals that detect GAMMA radiation. In the invention, this problem is solved by using an electromagnetic shield which comprises holes through which a focusing system makes the light emitted by the scintillator crystals go through. In addition, since the scintillator crystals of the GAMMA detector do not interfere with the static B0 field or the RF field of the RF coil, a compact design that allows placing the scintillator crystals within the RF field, thus minimizing the size of the GAMMA/RF device has been devised.

On the other hand, the GAMMA/RF system of the invention does not function independently but requires the prior existence of the fundamental elements of a conventional MR system, primarily B0 and gradient coils, although it also requires the processing software of the data acquired by the MR system, the outer capsule to prevent the escape of radiation into the room where the unit is located, and others that will be apparent to those skilled in the art upon reading the description of the invention. In addition, in the present document, it is understood that the subject of study can be not only the whole body of a human patient, but also a specific part of it as a particular organ, or a small animal. Finally, the terms "behind", "before" "after," and the like shall be interpreted according to the direction of the GAMMA radiation that radially passes through the GAMMA/RF device. In other words, it is understood that a part is located "before" another when it is located closer to the center of the device.

The GAMMA/RF system for PET-SPECT/MR imaging according to the present invention comprises a GAMMA/RF device that basically includes an RF coil and GAMMA radiation detector modules. As mentioned above, this GAMMA/RF device can be integrated into a conventional whole body MR, or it can be implemented as a portable device to acquire images of specific areas of the patient's body. The following describes each of the above components in greater detail:

a) RF Coil

It is understood that the RF coil considered belongs to the current state of the art systems used in MR, including coils for excitation and reception as well as combinations of coils that consist of one or more transmitting coils and one or more receiving coils. The latter are usually called "phased array" coils, while the "multi-element phased array" coils are able to acquire multiple channels of data in parallel.

The function of the RF coil of the invention is equivalent to that of an RF coil of a conventional MR system, but with a modified design which comprises some open spaces, formed by a thin, low density and atomic number material, allowing the passage of at least a significant part of GAMMA radiation generated inside. In a preferred embodiment of the invention, the RF coil is formed by a set of longitudinal bars joined at the ends, with the open spaces taking the form of parallelepiped. This is a structure similar to the "squirrel cage" used in the rotor of induction engines.

b) GAMMA Radiation Detector Modules

There is a plurality of GAMMA radiation detector modules placed radially around the RF coil, so as to form a cylinder, toroid or similar surrounding the object of study. In this context, the term "around" includes placing the modules either completely outside the RF coil, or partially inside through the open spaces of one of the possible embodiments of the RF coil, as the operation of the scintillator crystals used for the detection of GAMMA radiation is not affected by RF radiation.

The role of GAMMA radiation detector modules is equivalent to that of those used in a conventional PET-SPECT system, although with a structure, which will be described below, designed specifically for its integration with the RF coil.

In turn, each of the described GAMMA radiation detector modules comprises a scintillator crystal, a focusing system, an RF shielding layer and an array of photodetectors. The following describes each of them:

b1) Scintillator Crystal

This is a scintillation crystal of the type commonly used in conventional PET systems, which emits light flashes when it receives a GAMMA emission.

The scintillator crystals can be monolithic or pixelated. It is known that GAMMA radiation detectors that use pixelated crystals present inefficiencies due to the dead area between pixels. In addition, as GAMMA radiation detectors for PET systems require the simultaneous detection of two GAMMA rays in separate modules, the use of pixelated crystals decreases the efficiency of match events. In particular, it is estimated that sensitivity can be reduced by a factor of two in designs with pixelated crystals compared to other designs, while in systems with no requirement for matching this is reduced to up to 30%. Therefore, in a preferred embodiment of the invention the scintillator crystals are monolithic. In addition, monolithic scintillator crystals enhance the compactness of the GAMMA radiation detector modules, and therefore that of the GAMMA/RF device of the invention as a whole.

b2) Focusing System

The focusing system is an optical element having a first flat face coupled to the scintillator crystal and a second face comprising lenses that direct light onto an array of photodetectors. Its role is crucial in the present invention, as it focuses the light received from the scintillator crystal to which it is attached, and reaches its first face, creating a set of discrete foci directed to the photodetectors of an array of photodetectors that is facing its second face. Thus, if for example, the configuration of each lens (mainly shape and focus) is such that the total width of the outgoing light distribution coincides with the sensitive area of each photodetector, the loss of photons is avoided.

The shape and configuration of the lens can be any, as long as the function described is achieved, although in a preferred embodiment they are hemispherical lens.

In another embodiment of the invention, the GAMMA/RF device comprises one or more additional focusing systems located before the first one.

b3) RF Shielding Layer

The RF shielding layer serves to shield the array of photodetectors and its electronic "front end" from the RF field produced by the RF coil while allowing the passage of light produced in the scintillator crystal into the photo detectors of said array without significant loss of photons. This is achieved by introducing the RF shield in the focusing system off-peak (which represents dead zones thereof), so that there is no loss of light emitted from the scintillator crystal into the array of photodetectors.

For this, the RF shielding layer, which may be disposed between the focusing system and the array of photodetectors, is a plate that comprises openings through which the light focused by the focusing system passes into the array of photodetectors. In a particular embodiment of the invention, this is a metal grid with circular holes. In another particular embodiment, the RF shielding layer is a metal grid with square holes whose bars coincide with the interfocal spaces of the focusing system.

It is understood that a square grid with a distance between bars of about 3 mm should be sufficient to shield the field generated by the RF coil. However, a grid with smaller cells could be used if the photodetectors are also smaller, such as 1 mm photodetectors, and B0 magnetic fields of greater intensity. In the event that the size of the photodetectors does not match the size of the focusing system lens, the grid could be even smaller, defining a preferred range that goes from 10 microns to 6 mm grid size. Possible embodiments of the RF shielding layer are: a pure copper wire mesh or a thin and conductive copper sheet. In addition, in a preferred embodiment, the RF shielding layer can be created by a thin deposition of a metal film a few microns thick, on the focusing system.

The RF shielding layer should shield only the RF and not the gradient fields. Therefore, it should either be very thin (few microns), or eddy currents induced by the gradient field at low frequencies should be avoided through capacitances in the mesh. The simplest solution to reduce gradient eddy currents is a thin metal film or a copper sheet.

b4) Array of Photodetectors

This is an array of photodetectors that is sensitive to position. When arrays of photodetectors are used, the problem of the efficiency of photo detection arises, as the separations between them correspond to dead areas in which the photons are lost. The use of the focusing system of the invention solves this problem because the light is only focused in the direction of the photodetectors of the array, so there is no light loss.

According to a preferred embodiment of the invention, the photo detectors are silicon photomultipliers (SiPMT), which are insensitive to magnetic fields. In another preferred embodiment of the invention, the photo detectors are photomultipliers Type Micro Channel Plate PMTs, since they can operate in fields up to 2 Tesla. Most conventional MR systems operate with magnetic fields of 1.5 T, although increasingly more scanners are manufactured with higher magnetic field strengths.

b5) "Front End" Processing Means

These "front-end" processing means, typically a circuit board, carry out an initial processing of the signals generated by the photodetectors.

The GAMMA/RF system of the invention can be manufactured so that the size of the focusing system lenses coincides with that of the photodetectors, in which case the light focused by each lens would reach a single photodetector. Another possibility is that the lenses are smaller than the photodetectors, in which case the light of several lenses would reach the same photodetector.

In a particular embodiment of the invention, the GAMMA/RF system further comprises besides the GAMMA/RF, device, an external processing means to which signals obtained by the GAMMA/RF device are transmitted, and which is specifically designed to interpret said signals and determine the origin of the GAMMA radiation received. The external processing means may be integrated into the conventional MR system or could be a separate processing means.

However, a problem can arise when transmitting signals from GAMMA radiation detectors to the external processing means, which may be located outside the MR system's electromagnetic fields, or even out of the room protected by the MR system's Faraday cage. The reason is the exposure to strong static magnetic fields, variable field gradients and RF fields, which can affect said signals.

To resolve this problem, in a particular embodiment of the invention, analog differential signals in compensated lines are used. This allows the differential receiver of the processing means to reject external common mode interference and effectively reduces the noise induced from the RF fields and the connected gradients.

Alternatively, in another preferred embodiment of the invention, GAMMA radiation detector modules of the GAMMA/RF integrated portable device further comprise analog-digital converters, so that signals that are transmitted to the external processing module are digital instead of analog, e.g. low voltage differential signaling (LVDS). In this case, it will be necessary to shield the digital electronics so as not to affect the RF fields of the MR.

In addition, digital signals can easily be converted into optical signals so in another preferred embodiment, the GAMMA radiation detector modules of the invention further comprise means for transforming digital signals into optical. This solution will completely solve the problem of signal transmission between the integrated portable GAMMA/RF device and the external processing means, since the optical signals are completely immune to magnetic fields.

In addition, in another particular embodiment of the invention the GAMMA/RF hybrid system of the invention allows "gated acquisition", wherein "gated acquisition" refers to the fact that the electronic media associated with GAMMA radiation detector modules ("front-end" electronics, analog-digital conversion means, digital-optical conversion means besides other processing and/or acquisition means not specifically mentioned herein), are inactive during one or more time intervals. This allows preventing erroneous data acquisition from the GAMMA detector modules and its associated electronics during inappropriate time intervals. It also prevents the GAMMA/RF system from impairing the acquisition sequence of the conventional MR system. For these reasons, it is preferable that the aforementioned means remain inactive during the RF fields and the "switching" of the MR gradient, since they are only active during a short time of the operation cycle. Therefore, only a small fraction of GAMMA events in coincidence will be lost.

As previously mentioned, the portable version of the GAMMA/RF device described could be implemented from a portable RF coil of a conventional MR system without much modification, providing a compact system, this is, it does not significantly increase the size of the conventional MR system RF coil. For example, according to the invention, the size of a portable GAMMA/RF device dedicated to brain studies should be approximately 26 cm in the inner diameter and 32 cm in the outer diameter, which is the typical size of the conventional MR systems portable RF coils. Therefore, the portable GAMMA/RF device of the invention should take about 3 cm. However, the sensitivity of the images obtained by the conventional MR system from the RF coil data deteriorates considerably if the layer of RF shielding is placed very close to the RF coil. Therefore, it is estimated that the distance between the RF coil and the RF shielding layer should be greater than about 15 mm. This implies that the portable GAMMA/RF system will take at least 15 mm plus the total or partial length of the GAMMA radiation detector module of the invention.

It is relatively easy to replace the conventional RF coil by the portable GAMMA/RF device of the invention. It would therefore be relatively easy to improve the performance of thousands of MR systems already installed in the world. Since most of magnetic resonances are performed in a specific area of the body, the GAMMA/RF system in its portable version would be very useful in fields such as neurology, psychiatry and neuroscience in general. Moreover, its portability would allow its use in different conventional MR systems in a same facility, which would achieve considerable savings.

In addition, the metabolic information obtained by the PET-SPECT technique from the information acquired by the portable GAMMA/RF device of the invention is more sensitive than the one from other PET-SPECT/MR systems since the GAMMA radiation detector modules and the RF coil are located closer to the object of study. In addition, the total cost of a portable GAMMA/RF device of small dimensions is less than that of a whole body chamber due to the smaller number of GAMMA radiation detector modules required.

DESCRIPTION OF THE DRAWINGS

In order to help better understand the features of the invention, a set of drawings is attached as an integral part of said description, wherein the following is shown as way of illustration but not limited to.

DESCRIPTION OF PREFERRED EMBODIMENTS

Described below are some examples of embodiments of the GAMMA/RF system (1) according to the invention.

Figure 1:
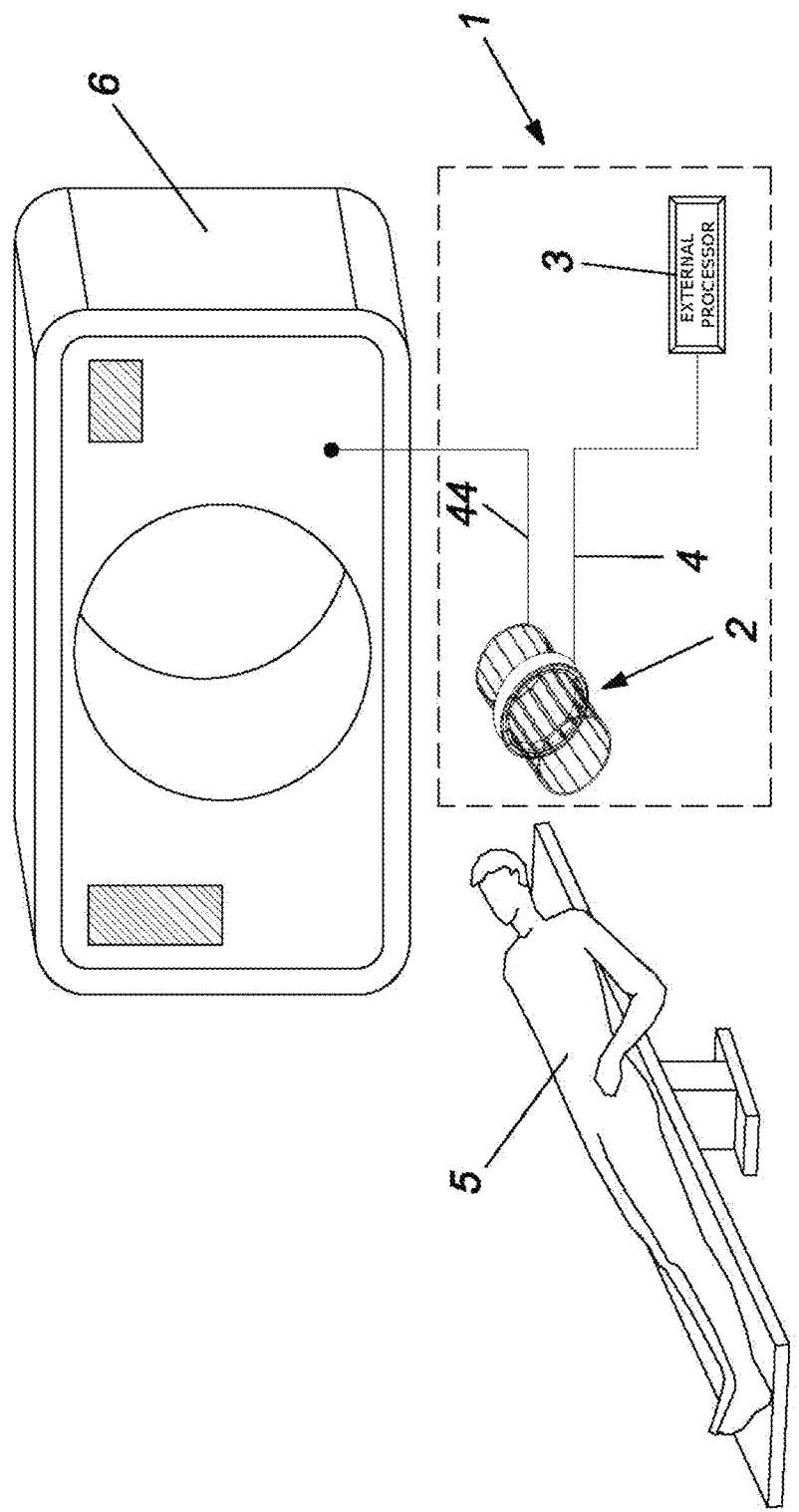
FIG. 1: Shows the compact, hybrid and integrated GAMMA/RF system of the invention, in its portable version, during its use in conjunction with a conventional MR system.

FIG. 1 shows an example of the GAMMA/RF system (1), which is formed by a GAMMA/RF device (2) in its portable version, and an external processing means (3), connected by a connection cable (4). Magnetic resonance signals generated in the portable GAMMA/RF device (2) are transmitted in the usual way, through the connection cable (44) available in conventional MR units when using a portable RF coil. In this example, the portable GAMMA/RF device (2) is placed on the patient's (5) head or ROI (region of interest, according to its acronym in English), then entering the patient (5) or animal inside a conventional MR system (6), via a mobile stretcher. The GAMMA/RF system (1) in combination with the conventional MR system (6) (which can be opened or closed, for MRI, MRS and NMR) obtains data that allows recording PET-SPECT and MR images simultaneously forming a final combined PET or SPECT and MR image. The data coming from some GAMMA radiation detector modules (8) pass through the connection cable (44), while the signals from the RF coil (7) pass through the connection cable (44). Both data are processed to obtain the SPECT and PET-MR combined image.

Figure 2A:
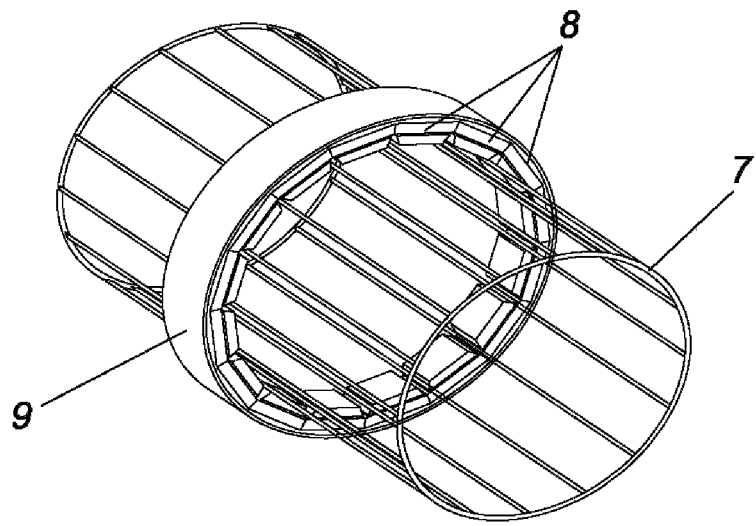
FIGS. 2a and 2b: Respectively show a perspective view and a cross section of the portable GAMMA/RF device of the invention.
Figure 2B:
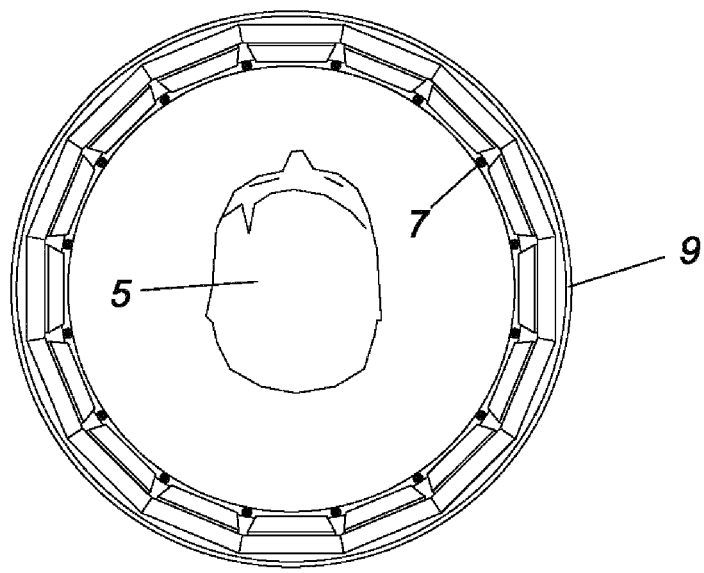

FIGS. 2a and 2b show respectively a perspective and a cross section of the portable GAMMA/RF device (2) of the invention, where the structural elements that compose it are shown:

a) An RF coil (7), of the resonator type in a "squirrel cage" shape, which consists of a set of longitudinal bars or wires attached to two rings at the ends, so that there are a few open spaces that allow the passage of GAMMA radiation coming, in this example, from the patient's (5) head. The invention does not restrict the use to other types of RF coils.

b) A set of GAMMA radiation detector modules (8) arranged radially forming a cylinder in the open spaces left by the RF coil (7) strands. In this example, there are 16 GAMMA radiation detector modules (8) arranged outside the RF coil (7), although as mentioned earlier in this document, it would be possible to arrange them in a more internal position among each pair of longitudinal strands. Thus, the detection dead area between two modules is used to place the RF coil strands. This design has the advantage of the GAMMA radiation that is directed to the detector modules (8) not suffering dispersion due to the RF coil (7) strands.

Figure 3A:
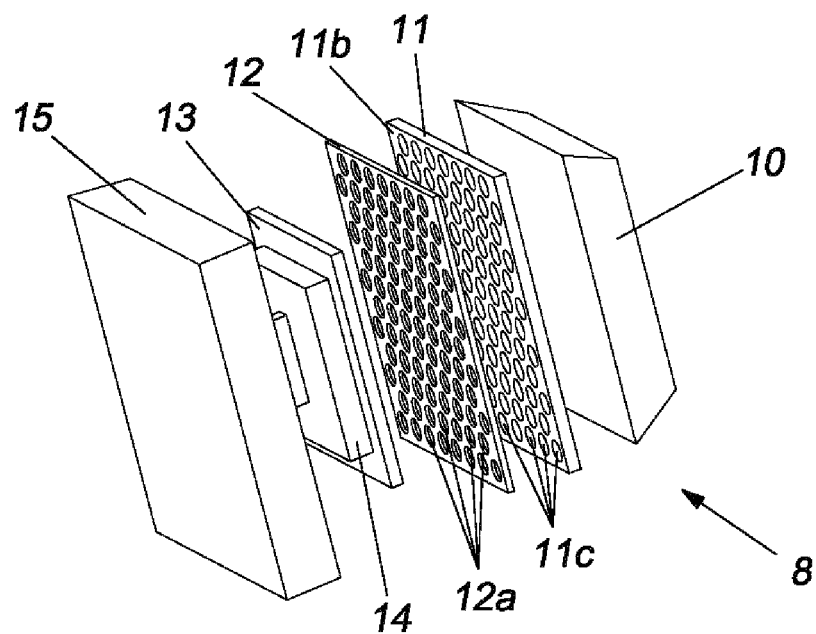
FIGS. 3a and 3b: Show respective exploded views of a GAMMA radiation detector module in accordance with an embodiment of the invention.
Figure 3B:
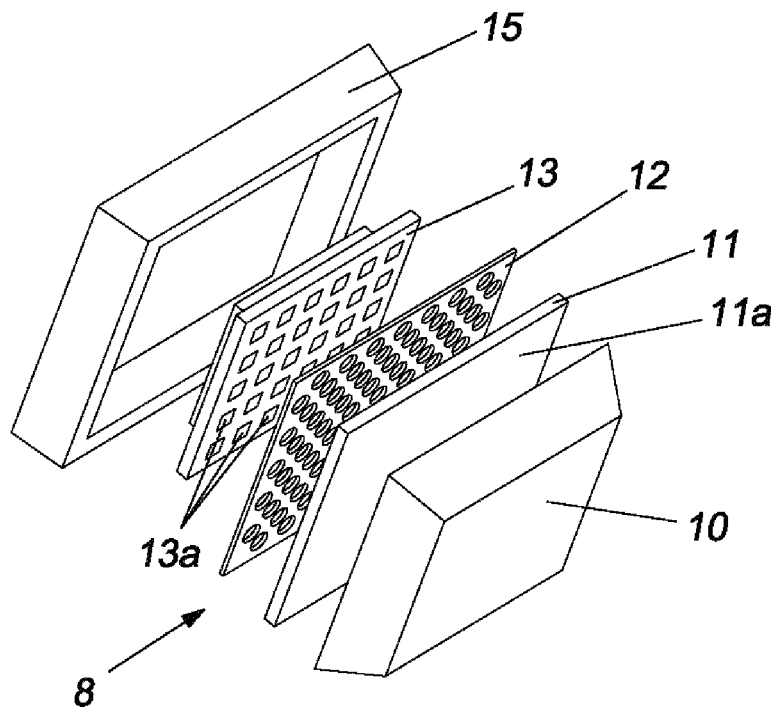

In this example, an external capsule (9) which provides an additional RF shielding and a support for installing the GAMMA detector modules (8) is shown. FIGS. 3a and 3b show in greater detail the internal structure of each GAMMA radiation detector module (8) of the present example. Each consists of:

A scintillator crystal (10) which receives the GAMMA radiation that comes from the patient (5) and converts it into light;

A focusing system (11) coupled to the scintillator crystal (10), which receives light from the scintillator crystal (10) and focuses it into an array (13) of photodetectors (13a). The focusing system (11), as described earlier in this document may be any shape provided it has a flat first face (11a) capable of receiving all the light of the scintillator crystal (10) and a second face (11b) able to focus all the light into the array (13) of photodetectors (13a). In this first example, the second face (11b) comprises an array of lenses (11c) in a hemispherical form, each of which focuses light onto a photodetector (13a) of the matrix, which in this example are of SiPMT type.

An RF shielding layer (12), placed between the focusing system (11) and the array (13) of photodetectors (13a), comprising circular holes (12a) through which light focused by each lens (11c) goes to each photodetector (13a).

FIGS. 3a and 3b also show a "front-end" processing means (14), which in this case consists of a circuit board disposed in the back face of the array (13) of photodetectors (13a), which acquire and process the signals of photodetectors (13a) before being sent to the external processing means (3) of FIG. 1 For example, the electronic board could make the analog-digital conversion of data, as explained earlier in this document. Finally, a cover (15) protects the components of each GAMMA radiation detector module (8).

Figure 4:
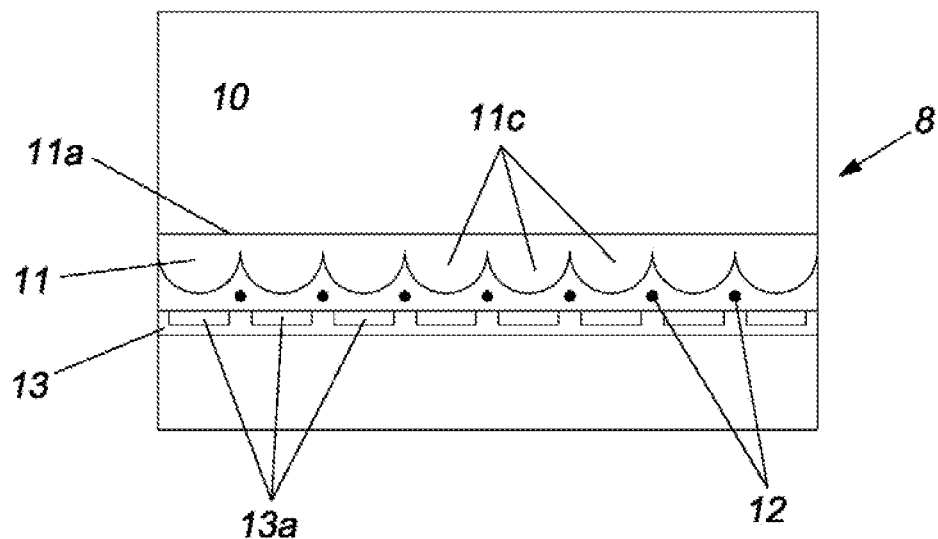
FIG. 4: Shows a cross section of an embodiment of the GAMMA radiation detector module of the invention where a single focusing system with RF shielding and a single monolithic scintillator crystal are used.
Figure 5:
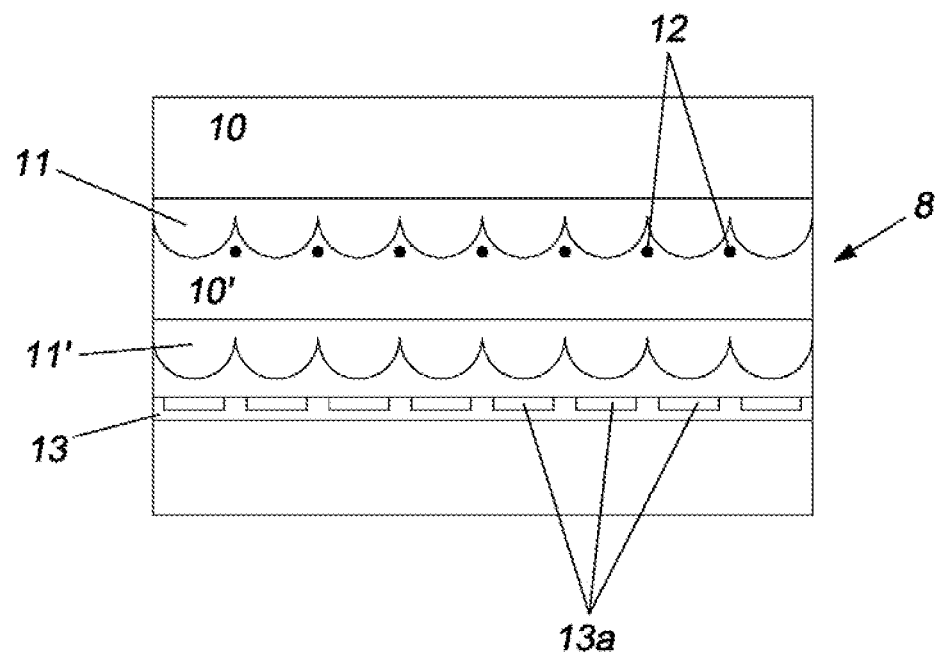
FIG. 5: Shows a cross section of a second embodiment of the GAMMA radiation detector module of the invention wherein two focusing systems, one of them with at least an RF shielding and two monolithic scintillator crystals are used.

FIG. 4 shows a cross section of a particular embodiment of a GAMMA radiation detector module (8) according to the invention, which shows how the entire surface of the first face (11a) of the microlens (11) receives the light emitted by the crystal scintillator (10) and focuses it only on the photodetectors (13a). In this case, interfocal spaces are used to arrange the RF shielding layer (12), which in this example is a grid. FIG. 5 shows a second example of a GAMMA radiation detector module (8) in which a second scintillator crystal (10') and a second focusing system (11') have been arranged before the first ones.

Figure 6:
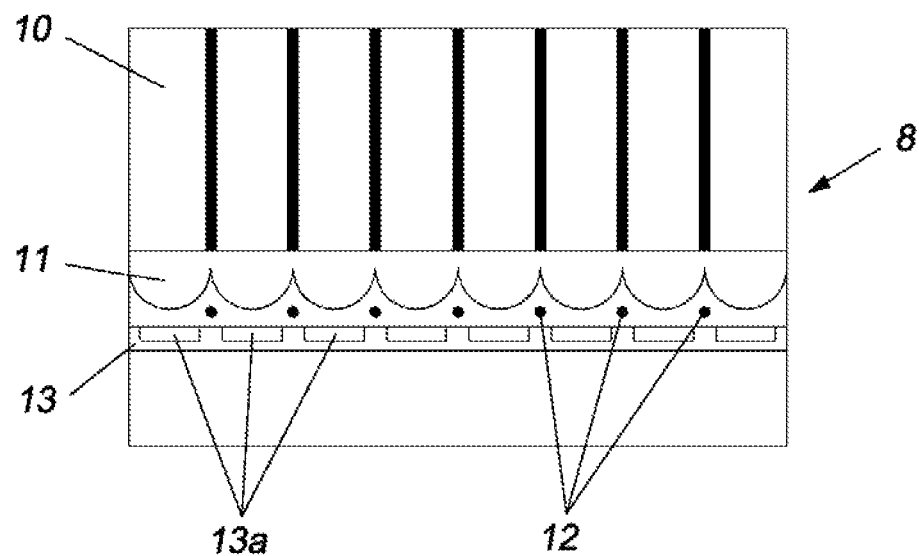
FIG. 6: Shows a cross section of a third embodiment of the GAMMA radiation detector module of the invention wherein a focusing system with RF shielding and a pixelated scintillator crystal are used.
Figure 7:
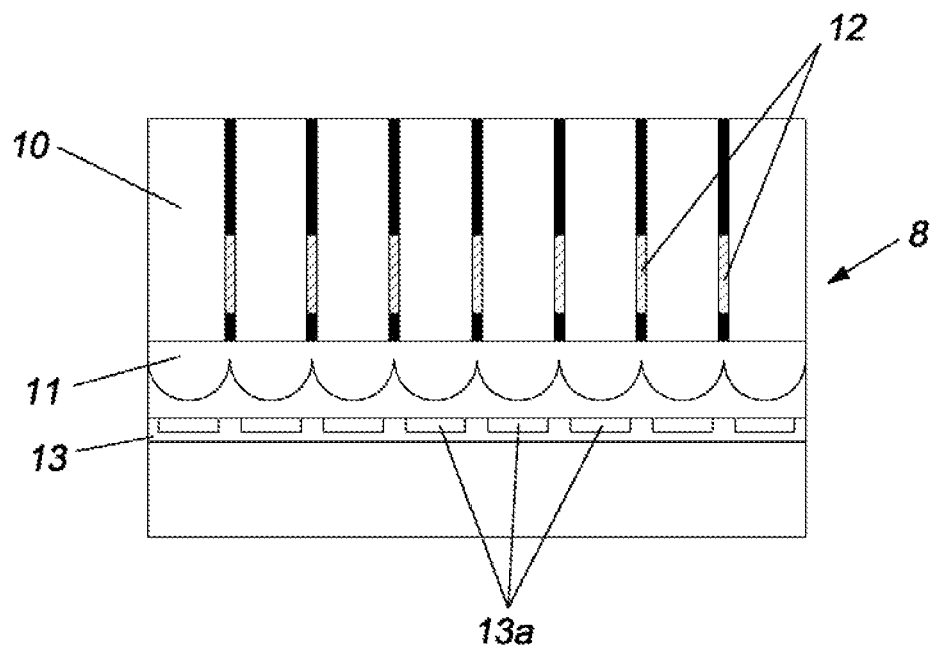
FIG. 7: Shows a cross section of a fourth embodiment of the GAMMA radiation detector module of the invention where a focusing system and a pixelated scintillator crystal among which the RF shield is inserted, are used.

FIGS. 6 and 7 show respective sections of GAMMA radiation detector modules (8) where pixelated scintillator crystals (10) have been used. In FIG. 6, the RF shielding layer (12) has a grid shape whose size is matched to the size of the pixelated scintillator crystal pixels (10), and is arranged between the focusing system (11) and the array (13) of photodetectors (13a). FIG. 7, on the other hand, shows an RF shielding layer (12) embedded in the separation between the crystals of a pixelated scintillator crystal (10).

Figure 8:
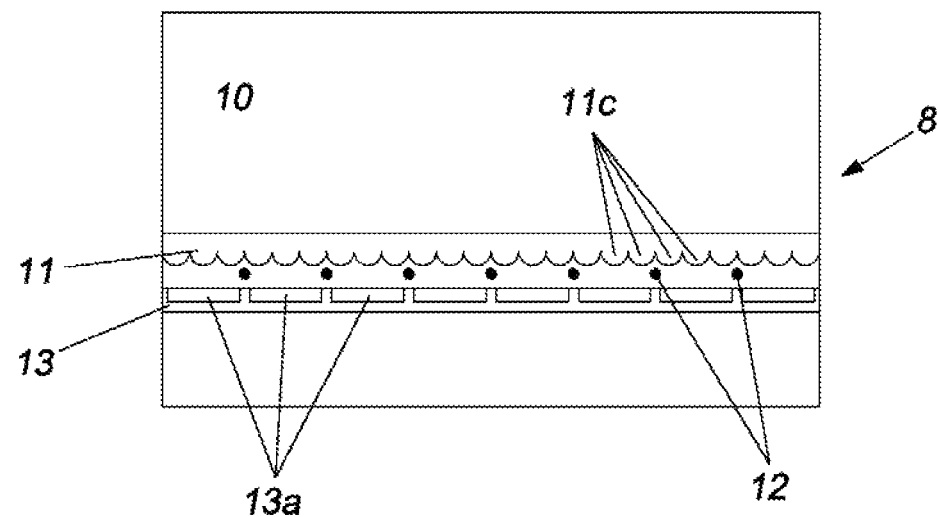
FIG. 8: Shows a cross section of a fifth embodiment of the GAMMA radiation detector module of the invention, where the focusing system lenses and the RF shielding grid have a different size to that of the photodetectors in the case of a monolithic block.
Figure 9:
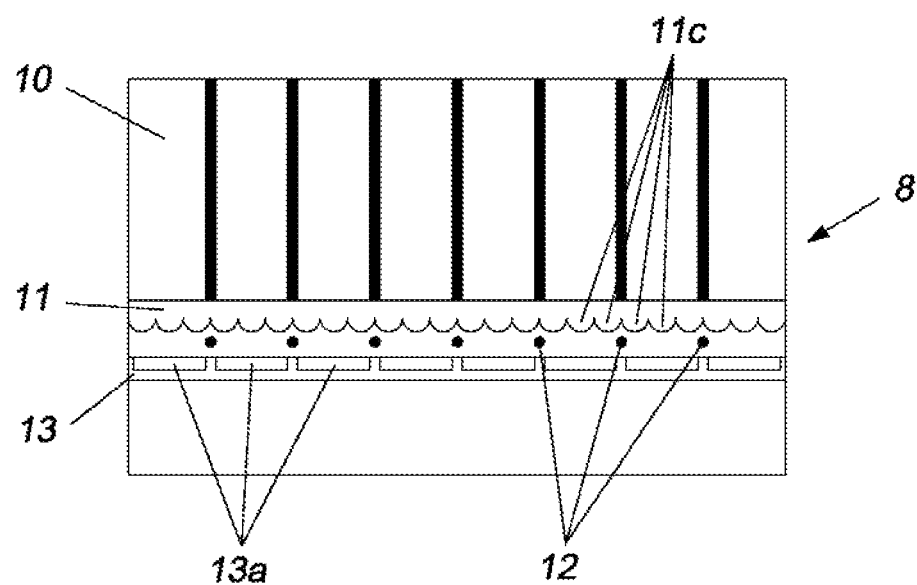
FIG. 9: Shows a cross section of a sixth embodiment of the GAMMA radiation detector module of the invention, wherein the focusing system lenses and the RF shielding grid have a different size to that of the photodetectors in the case of a pixelated scintillator crystal.

Finally, FIGS. 8 and 9 show respective sections of GAMMA radiation detector modules (8) where the size of the lenses (11c) of the focusing system (11) and the grid of the RF shielding layer (12) do not match the size of the photodetectors (13a). In both cases (monolithic or pixelated scintillator crystal (10)) it should be noted that the grid size (distance between bars) of the RF shielding layer (12) does not have to match the interfocal distance of the focusing system (11), and it could be equal or higher (an integer number of times), than these interfocal spaces. On the other hand, the embodiment corresponding to FIG. 8 can be extended to the case in which two or more monolithic blocks are used.

The invention claimed is:

1. A GAMMA/RF compact, hybrid and integrated system for PET-SPECT/MR simultaneous imaging, having a GAMMA/RF device comprising:
 an RF coil comprising spaces that allow a passage of at least a significant part of a GAMMA radiation generated internally; and
 a set of GAMMA radiation detector modules arranged radially around the RF coil, wherein each GAMMA radiation detector module comprises:
  a scintillator crystal configured to emit light when it receives GAMMA emission,
  a focusing system comprising:
   a first face coupled to the scintillator crystal configured to receive the light, and
   a second face comprising:
    lenses configured to focus the light received from the scintillator crystal to photodetectors of an array of photodetectors, wherein a configuration of the lens is such that the total width of the focused light coincides with each photodetector, and
    spaces between lenses which are dead zones of the focusing system,
  an RF shielding layer, placed between the focusing system and the array of the photodetectors, comprising circular holes aligned with the respective lenses, wherein each of the circular holes is configured to allow the focused light from respective ones of the lenses to pass through to the respective photodetectors, wherein the RF shielding layer provides shielding in the dead zones of the focusing system,
  the array of the photodetectors placed behind the RF shielding layer so as to receive the light, faced to the second face of the focusing system, and
  a processor configured to process signals generated by the photodetectors.

2. The system according to claim 1, wherein the RF coil is formed by a set of longitudinal bars attached with a ring at each end so as to comprise some openings in a parallelepiped shape.

3. The system according to claim 1, wherein the RF coil comprises spaces formed by a thin, low density and low atomic number material that allows the passage of at least the significant part of GAMMA radiation.

4. The system according to claim 1, wherein the scintillator crystals are monolithic.

5. The system according to claim 1, wherein the scintillator crystals are pixelated.

6. The system according to claim 1, wherein a size of the lenses of the focusing system matches a size of the photodetectors.

7. The system according to claim 1, wherein a size of the lenses of the focusing system does not match a size of the photodetectors.

8. The system according to claim 1, wherein the lenses of the focusing system have a hemispherical shape.

9. The system according to claim 1, wherein the set of GAMMA radiation detector modules further comprise an additional scintillator crystal and an additional focusing system arranged before the scintillator crystal and the focusing system.

10. The system according to claim 1, wherein the RF shield layer is a metal grid with circular holes.

11. The system according to claim 1, wherein the RF shield layer is a metal grid with square holes.

12. The system according to claim 11, wherein the grid mesh is between 10 microns and 6 mm.

13. The system according to claim 1, wherein the RF shield layer is a chemical deposition of a thin metal film.

14. The system according to claim 1, wherein the photodetectors are chosen from a group consisting of the following: silicon photomultipliers (SiPMT) and Micro Channel Plate (PMT) type.

15. The system according to claim 1, wherein the GAMMA/RF device is portable.

16. The system according to claim 15, wherein a distance between the RF coil and the RF shielding layer is greater than 15 mm.

17. The system according to claim 1, further comprising an external processor coupled with the GAMMA/RF device by a cable, which is configured to receive and interpret GAMMA signals obtained by the GAMMA/RF device.

18. The system according to claim 17, wherein the GAMMA/RF device further comprises analog-digital converters configured to allow a transmission of digital signals to the external processor.

19. The system according to claim 17, wherein the GAMMA/RF device further comprises digital-optical converters configured to allow a transmission of optical signals to the external processor.

20. The system according to claim 17, wherein the system is configured to perform gated-acquisition.

* * * * *